(12) United States Patent
Bi

(10) Patent No.: US 6,571,609 B1
(45) Date of Patent: Jun. 3, 2003

(54) DIGITAL VISCOMETER WITH ARM AND FORCE SENSOR TO MEASURE TORQUE

(76) Inventor: Hongfeng Bi, 800 W. Sam Houston Pkwy., S., #107, Houston, TX (US) 77042

( * ) Notice: Subject to any disclaimer, the term of this patent is extended or adjusted under 35 U.S.C. 154(b) by 17 days.

(21) Appl. No.: 09/851,736

(22) Filed: May 9, 2001

(51) Int. Cl.⁷ .............................................. G01N 11/14
(52) U.S. Cl. .................. 73/54.31; 73/54.23; 73/54.28; 73/54.38
(58) Field of Search ............................. 73/54.01, 54.23, 73/54.28, 54.26, 54.38, 54.39, 54.31

(56) References Cited

U.S. PATENT DOCUMENTS

| | | |
|---|---|---|
| 2,703,006 A | 3/1955 | Savins |
| 3,435,666 A | 4/1969 | Fann .......................... 73/54.32 |
| 3,935,726 A | 2/1976 | Heinz ......................... 73/54.32 |
| 4,062,225 A | 12/1977 | Murphy, Jr. |
| 4,173,142 A * | 11/1979 | Heinz ......................... 73/54.32 |
| 4,347,734 A | 9/1982 | Heinz |
| 4,524,611 A | 6/1985 | Richon et al. |
| 4,571,988 A | 2/1986 | Murphy, Jr. |
| 4,630,468 A | 12/1986 | Sweet |
| 4,765,180 A | 8/1988 | Clifton |
| 4,878,377 A | 11/1989 | Abel .......................... 73/54.32 |
| 4,878,378 A * | 11/1989 | Harada ....................... 73/54.35 |
| 4,905,504 A * | 3/1990 | Carriere et al. ............. 73/54.39 |
| 5,350,567 A * | 9/1994 | Takeda et al. ............... 73/54.33 |
| 5,503,003 A | 4/1996 | Brookfield |
| 5,535,619 A | 7/1996 | Brookfield |
| 5,763,766 A | 6/1998 | Robinson |
| 5,792,942 A * | 8/1998 | Hosokawa ................... 73/54.35 |

FOREIGN PATENT DOCUMENTS

JP            4-54435    *  2/1992  ................ 73/54.28

* cited by examiner

Primary Examiner—Daniel S. Larkin

(57) ABSTRACT

Viscometer (2) with a sleeve (30) rotatable by a sprocket (20) and a timing belt (44) to shear a tested fluid thus imparting torque to a bob (28) mounted on a shaft (14) supported via axially spaced bearings (16, 22), an arm (12) connecting to the top of the shaft (14) applies force to a force sensor (10) which is proportional to the torque applied to the bob.

8 Claims, 2 Drawing Sheets

DIGITAL VISCOMETER WITH ARM AND FORCE SENSOR TO MEASURE TORQUE

CROSS-REFERENCE TO RELATED APPLICATIONS

Not applicable.

BACKGROUND

1. Field of Invention

The present invention relates to measurement of viscosity with a variable speed drive and force-sensing device.

2. Description of Prior Art

A liquid between two surfaces will shear when one surface moves relative to the other. The force needed to make such a movement is directly related to the viscosity of the liquid (with the mechanical configuration factored out). Viscometers typically rotate a cup or bob within a still cylinder with the liquid therebetween, or rotate an outer cylinder while keeping the inside coaxial bob inert. In such examples, torque is directly related to the viscosity of the liquid (again with mechanical configuration factored out).

Several types of arrangement have been applied to measure the torque due to the viscosity of the liquid. In U.S. Pat. No. 3,435,666, a spring is attached to the inside bob while driving the outer cylinder. The mechanical dial reading reflects the deflection of the spring, which in turn is proportional to the torque applied by the liquid. However, it is relatively expensive to convert the deflection of the spring to electronic signal for automatic data acquisition and control purpose. In U.S. Pat. No. 5,503,003, a spring connection between two slotted wheels, where one wheel is attached to a mechanism that is sensitive to the drag caused by a viscous liquid, and the other wheel is attached to a mechanical drive assembly. When operated, the wheel sensitive to drag deflects with respect to the driven wheel. Optical sensors detect the resulting deflection that is calibrated to indicate the viscosity of the liquid. The drawback of this arrangement is that the response time of the spring connection is relatively long and the spring connection is prone to overload damage.

It is an object of this invention to provide a reliable, but rugged and economical instrument with integrated electronics usable in viscosity measuring applications, under atmospheric, pressurized, lowland high temperature conditions.

It is another object to provide a viscometer that operates with a wide range of liquids with an extremely fast response.

It is another object of the invention to provide a viscometer that is economical to manufacture yet meets industry standards of accuracy, reliability, durability, dependability, and ease of maintenance and cleaning.

SUMMARY

The present invention provides a new and improved apparatus and method for measuring the viscosity of a fluid. The apparatus and method of the present invention are particularly useful for measuring the instant shear stress and viscosity of a liquid with viscoelasticity property, where a fast response time of measurement is essential. The apparatus is also particularly useful for accurately converting the torque applied by the liquid to electronic signals very economically. The present invention provides an apparatus and method for making fluid viscosity measurements employing an arm and an electronic force sensor.

A viscometer in accord with the present invention conveniently comprises a stationary frame from which a rotatable sleeve is suspended and includes a means for rotating the sleeve. Suspended within the sleeve is a bob capable of angular motion about the longitudinal axis of the sleeve. The device is constructed so that the bob and at least the portion of the sleeve near the bob may be immersed within the liquid, the viscosity of which is to be determined. The bob is suspended from the stationary frame by a low friction bearing which permits limited angular motion about its center of rotation. An arm is attached to the bob shaft or extended portion of the bob, and the arm is contacting an electronic force sensor. Given the known characteristics of the viscometer, the force applied on the force sensor is proportional to the viscosity of the liquid.

Alternative embodiments of the present method comprise a still sleeve, and rotate the bob through a force sensor and an arm.

The apparatus and method of the present invention provide a fast response, bi-directional, and economical way to measure the shear stress property of fluid under shear condition.

DRAWING FIGURES

Other objects, features, and advantages will be apparent from the following detailed description of preferred embodiments taken in conjunction with accompanying drawing in which.

REFERENCED NUMERALS IN DRAWINGS

Figure 1:
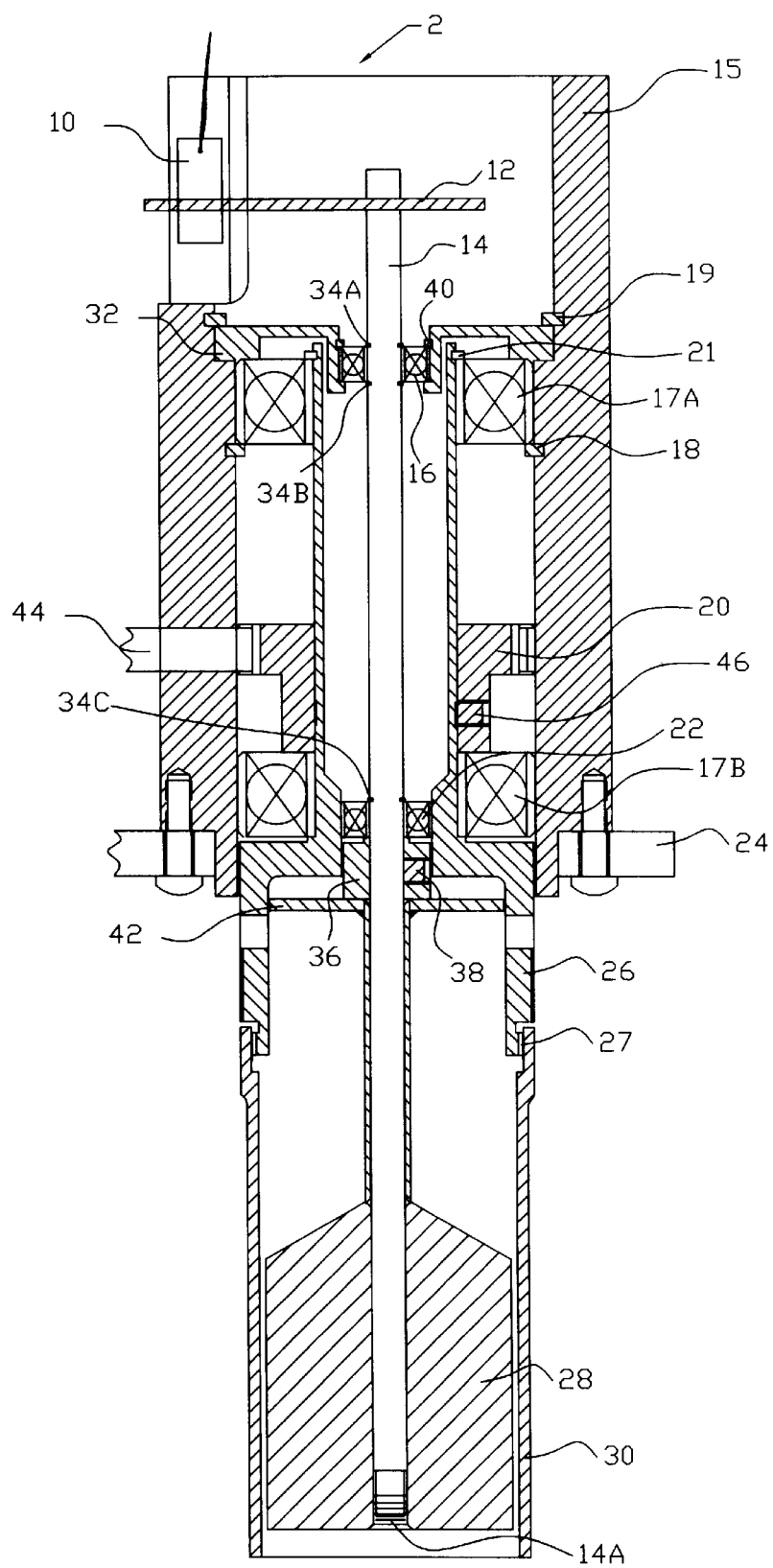
FIG. 1 is a cross-section view of a preferred embodiment of the invention.

| Reference Numerals In Drawings | |
|---|---|
| 10 force sensor | 12 arm |
| 14 bob shaft | 14A thread |
| 15 main frame | 16 shaft bearing (upper) |
| 17A upper main bearing | 17B lower main bearing |
| 18 snap ring | 19 snap ring |
| 20 sprocket | 21 snap ring |
| 22 shaft bearing (lower) | 24 support plate |
| 26 rotor | 27 thread |
| 28 bob | 30 sleeve |
| 32 upper bearing retainer | 34A snap ring |
| 34B snap ring | 34C snap ring |
| 36 bearing retainer | 38 set-in screw |
| 40 snap ring | 42 dust shield |
| 44 motor driven belt | 46 set-in screw |
| 48 strain gauge | 50 load cell |

DESCRIPTION

FIG. 1—Preferred Embodiment

FIG. 1 shows a cross-view of viscometer 2 with a bob 28 and outside sleeve 30. The lower part of the sleeve can be opened for allowing the bob 28 and sleeve 30 to be immersed into a liquid—the liquid's viscosity to be measured. Sleeve 30 could also have a closed end to hold a small amount of to-be measured fluid. Sleeve 30 is detachable from rotor 26 via screw thread 27. Rotor 26 is mounted on main frame 15 through axially spaced bearing 17A, 17B with bearing retainer rings 18 and 21. Two spaced bearings 17A and 17B are needed for alignment. Sprocket 20 is pushed against bearing 17B and is secured to rotor 26 by set-in screw 46. Motor-driven timing belt 44 transmits the power to turn sprocket 20. Main Frame 15 and a motor are mounted to support plate 24.

Upper bearing retainer 32 pushes against bearing 17A and is locked to main frame 15 with snap ring 21. Shaft 14 is coaxially mounted respect to rotor 26 through axially spaced bearing 22 and 16 with bearing retainer rings 34A, 34B, 34C. Bearing retainer 36 is secured to shaft 14 with setscrew 38. The gap between bearing retainer 36 and rotor 26 is about 0.003 inches. This tight shaft clearance impedes vapor penetration therethrough.

Arm 12 is attached to shaft 14 through a drilled hole on shaft 14. Arm 12 can apply force to a force sensor 10. Force sensor 10 could be a strain gauge, load cell, or other types of sensors that can convert the instant force information to electronic signals. Force sensor 10 could be measuring one direction or bi-direction force applied by the arm 14.

The bob 28 is coaxially supported from a 3/32" shaft 14 by thread 14A.

Figure 2:
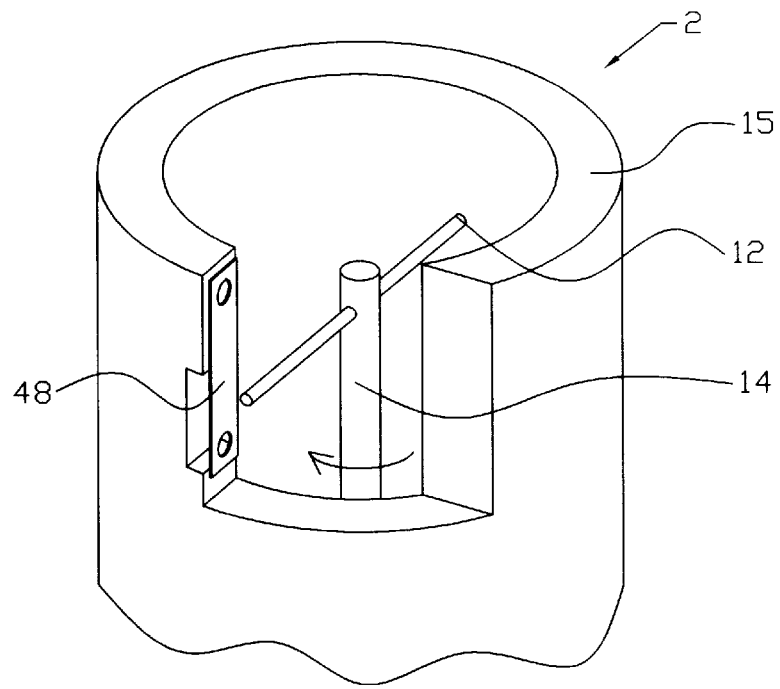
FIG. 2 is an isometric view of the force sensor and its mounting details when force sensor is a strain gauge.

FIG. 2—Force Sensor is a Strain Gauge Embodiment

FIG. 2 is an isometric view of the top portion of the viscometer 2 when the force sensor 10 is a strain gauge 48. Strain gauge 48 is fixed on main frame 15 by using either glue or bolts. Arm 12, bob shaft 14, and bob 28 can rotate corresponding to the axis of bob 28 freely within some degree, until arm 12 contacts strain gauge 48 or main body 15. Once arm 12 contacts strain gauge 48, strain gauge 48 prevents any further counter clockwise rotation of arm 12, bob shaft 14, and bob 28. If arm 12 is glued to or fixed on strain gauge 48, strain gauge 48 will prevent the rotation of arm 12, bob shaft 14, and bob 28 in both counter clockwise and clockwise directions.

Figure 3:
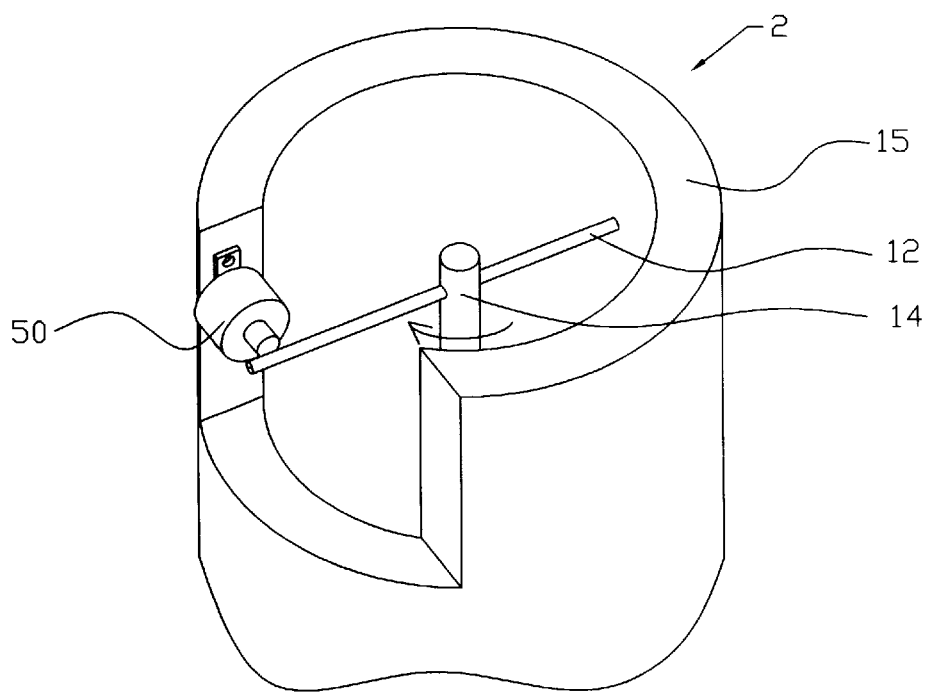
FIG. 3 is an isometric view of the force sensor and its mounting details when force sensor is a load cell.

FIG. 3—Force Sensor is a Load Cell Embodiment

FIG. 3 is an isometric view of the top portion of the viscometer 2 when the force sensor is a load cell 50. Load cell 50 is fixed on main frame 15 by using either glue or bolts. Arm 12, bob shaft 14 and bob 28 can rotate corresponding to the axis of bob 28 freely within some degree, until arm 12 contacts load cell 50 or main body 15. Once arm 12 contacts load cell 50, load cell 50 prevents any further counter clockwise rotation of arm 12, bob shaft 14, and bob 28. If arm 12 is glued to or fixed together with load cell 50, load cell 50 will prevent the rotation of arm 12, bob shaft 14, and bob 28 in both counter clockwise and clockwise directions.

Advantages

From the description above, a number of advantages of my viscometer become evident:

(a) Very economically converting torque to electronic signal.

(b) Very robust structure can handle extremely overload. Because it is very easy to find a force sensor in the market which has an overload capacity of 50 times or more of its measurement range, the viscometer can easily achieve overload capacity of 50 times or more of its measurement range.

(c) Extremely fast response. Since force sensors normally can be used with tiny deflection under load, the transient shear stress change under shear rate can be recorded.

(d) When using force sensors that can measure bi-directional load, i.e. pull or press force, this invention can measure visco-elasticity of fluid under dynamic vibrating movement.

Operation—FIGS. 1, 2, 3

During operation, a motor drives the sprocket 20 through timing belt 44 rotating in a counter clockwise direction. Thus, rotor 26 rotates together with sprocket 20 in a counter clockwise direction. Sleeve 30 has the same rotation as rotor 26 since they are attached through thread 27. Since bob 28 is still, the shear rate between the sleeve 30 and bob 28 will cause a shear stress from the liquid (under most condition, this shear stress is due to viscosity of the liquid). The shear stress generates a counter clockwise directional torque applying on bob 28. Since bob 28 is connected to shaft 14, a counter clockwise a directional torque will be applied to shaft 14. Because bob shaft 14 is connected to arm 12, once force sensor 10 contacts arm 12, force sensor 10 prevents any further counter clockwise rotation of arm 12, bob shaft 14, and bob 28. At the same time, arm 12 will apply a force on force sensor 10. This force equals the counter clockwise torque applied on bob 28 divided by the projected distance from the axis of the bob shaft 14 to force sensor 10 contacting point. This distance in turn is a constant. Force sensor 10 converts the force signals to electronic signals for further data acquisition and processing.

Conclusion, Ramifications, and Scope

Accordingly, the reader will see that this invention can be used to construct an economical electronic viscometer easily. A ramification of the preferred embodiment is that arm 12 is fixed on force sensor 10, and force sensor 10 stops the rotation of arm 12 in both clockwise and counter clockwise directions. Therefor force sensor 10 can measure both clockwise and counter clockwise directional torque applied on bob 28. The fast response and bi-directional measurement capability of this invention also makes sophisticated transient measurement of liquid property easy. Another ramification of the preferred embodiment is that bob 28 and bob shaft 14 can be an integrated part. So said integrated part serves as a bob and is directly connected to arm 12. Another ramification of the preferred embodiment is that bob 28 does not have to be cylindrical shaped. Bob 28 could be shaped like a plate, a square, or other shapes. Another ramification of the preferred embodiment is that the rotation axis of bob 28 and bob shaft 14 does not have to be the same rotation axis of rotor 26. The rotation axis of bob 28 and bob shaft 14 could be parallel to the rotation axis of the rotor 26.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including, the doctrine of equivalents.

What I claimed:

1. Viscometer instrument comprising:
   (a) a rotor which is driven to rotate while contacting with a sample liquid to be measured,
   (b) means for driving said rotor to rotate,
   (c) a bob within said rotor,
   (d) means for suspending said bob therefor, said bob can rotate corresponding to an axis which is parallel to or the same as the axis that said rotor is rotating,
   (e) an arm indirectly or directly connecting to a portion of said bob, and rotates together with said bob, and (f) means for stopping the rotation of said arm, said means also has the capability of converting a force to an electronic signal, wherein said electronic signal is changed to viscosity of said sample liquid.

2. The instrument of claim 1 wherein said means to convert a force to an electronic signal is a strain gauge.

3. The instrument of claim 2 wherein the bob is suspended with a bob shaft which in turn is mounted via axially spaced bearing means.

4. The instrument of claim 3 wherein said rotor and said bob are cylindrical shaped.

5. The instrument of claim 1 wherein said means to convert a force to an electronic signal is a load cell.

6. The instrument of claim 5 wherein the bob is suspended with a bob shaft which in turn is mounted via axially spaced bearing means.

7. The instrument of claim 6 wherein said rotor and said bob are cylindrical shaped.

8. The instrument of claim 1 wherein said rotor and said bob are cylindrical shaped.

* * * * *